(12) United States Patent
Yakovenko

(10) Patent No.: US 6,969,604 B1
(45) Date of Patent: Nov. 29, 2005

(54) ELECTROPORATION CHAMBER

(76) Inventor: Sergey A. Yakovenko, Kolomensky proezd, 8/3-299, Moscow, 115446 (RU)

(*) Notice: Subject to any disclaimer, the term of this patent is extended or adjusted under 35 U.S.C. 154(b) by 0 days.

(21) Appl. No.: 10/872,242

(22) Filed: Jun. 18, 2004

Related U.S. Application Data

(60) Provisional application No. 60/480,484, filed on Jun. 20, 2003.

(51) Int. Cl.[7] ............................................. C12M 1/42
(52) U.S. Cl. ........................ 435/285.2; 435/288.1; 204/403.01; 204/403.02
(58) Field of Search ................... 435/173.5, 173.6, 435/285.2, 288.1; 204/403.1, 403.02

(56) References Cited

U.S. PATENT DOCUMENTS

| | | | |
|---|---|---|---|
| 4,476,004 A | 10/1984 | Pohl | |
| 4,511,659 A | * 4/1985 | Matson | 205/780.5 |
| 4,594,138 A | * 6/1986 | Thompson | 204/665 |
| 4,923,814 A | 5/1990 | Marshall, III | |
| 5,545,130 A | 8/1996 | Hofmann et al. | |
| 5,676,646 A | 10/1997 | Hofmann et al. | |
| 5,720,921 A | 2/1998 | Meserol | |
| 5,869,326 A | 2/1999 | Hofmann | |
| 5,911,223 A | 6/1999 | Weaver et al. | |
| 5,983,131 A | 11/1999 | Weaver et al. | |
| 5,989,901 A | 11/1999 | Zhao et al. | |
| 6,010,613 A | 1/2000 | Walters et al. | |
| 6,014,584 A | 1/2000 | Hofmann et al. | |
| 6,027,488 A | 2/2000 | Hofmann et al. | |
| 6,043,066 A | 3/2000 | Mangano et al. | |
| 6,068,650 A | 5/2000 | Hofmann et al. | |
| 6,074,605 A | 6/2000 | Meserol et al. | |
| 6,090,617 A | 7/2000 | Meserol | |
| 6,096,020 A | 8/2000 | Hofmann | |
| 6,103,084 A | 8/2000 | Uhen | |
| 6,150,148 A | 11/2000 | Nanda et al. | |
| 6,300,108 B1 | 10/2001 | Rubinsky et al. | |
| 6,403,348 B1 | 6/2002 | Rubinsky et al. | |
| 6,562,604 B2 | 5/2003 | Rubinsky et al. | |
| 6,661,575 B1 | 12/2003 | Yakovenko | |
| 6,746,441 B1 | 6/2004 | Hofmann et al. | |

OTHER PUBLICATIONS

Zimmerman, Ulrich; Neil, G.A., Electromanipulation of cells, CRC Press (1995), pp. 192-197, 232-233, 238-239, 242-243, 272-273, 308-309 and 312-313.

* cited by examiner

*Primary Examiner*—David Redding
(74) *Attorney, Agent, or Firm*—Craig A. Fieschko, Esq.; DeWitt Ross & Stevens S.C.

(57) ABSTRACT

An electroporation chamber is provided wherein cells are borne by a fluid medium through a conductive mesh receiving electrode (with the mesh size being such that it allows passage of cells of the desired size/type) and into the chamber. The cells are then captured on a conductive mesh capturing electrode having a mesh size which retains the desired cells. The electrodes are then charged to effect electroporation or other operations within the captured cells between the electrodes. If desired, different fluid media may flow through the electrodes and chamber (and over the cells) during such activities. When operations are completed, fluid flow may be reversed to carry the treated cells back out of the chamber through the receiving electrode.

20 Claims, 1 Drawing Sheet

US 6,969,604 B1

ELECTROPORATION CHAMBER

CROSS-REFERENCE TO RELATED APPLICATIONS

This application claims priority under 35 USC §119(e) to U.S. Provisional Patent Application 60/480,484 filed 20 Jun. 2003, the entirety of which is incorporated by reference herein.

FIELD OF THE INVENTION

This document concerns an invention relating generally to electroporation chambers, and more specifically to flow-through electroporation chambers.

BACKGROUND OF THE INVENTION

Electroporation chambers are used to apply electric pulses to cells to open their membranes, thereby allowing the performance of various operations such as the introduction of materials (e.g., genetic materials, ions, and chemical agents such as drugs), the activation of cell processes (e.g., the activation of oocyte development), and the electrofusion of cells (a process whereby porated cells are merged into a single cell). General background information on electroporators (i.e., devices which include chambers wherein electroporation occurs) and electroporation procedures can be found in, for example, U.S. Pat. No. 4,476,004 to Pohl; U.S. Pat. No. 4,923,814 to Marshall, III; U.S. Pat. No. 5,869,326 to Hofmann; U.S. Pat. No. 5,911,223 to Weaver et al.; U.S. Pat. No. 5,983,131 to Weaver et al.; U.S. Pat. No. 5,989,901 to Zhao et al.; U.S. Pat. No. 6,010,613 to Walters et al.; U.S. Pat. No. 6,014,584 to Hoffman et al.; U.S. Pat. No. 6,043,066 to Mangano et al.; U.S. Pat. No. 6,068,650 to Hoffman et al.; U.S. Pat. No. 6,096,020 to Hoffman; U.S. Pat. No. 6,103,084 to Uhen; U.S. Pat. No. 6,150,148 to Nanda et al.; and in the references cited therein. For greater productivity, flow-through electroporation chambers have been developed, as in U.S. Pat. No. 6,027,488 to Hoffman et al. and U.S. Pat. Nos. 6,300,108, 6,403,348, and 6,562,604 to Rubinsky et al. Nevertheless, electroporation procedures remain challenging to perform, in large part owing to difficulties with manipulating cells (in view of their size and fragility), and the controlled environments in which procedures must be performed.

SUMMARY OF THE INVENTION

The invention, which is defined by the claims set forth at the end of this document, is directed to electroporation chambers and electroporation procedures which at least partially alleviate the difficulties with prior devices and methods. A basic understanding of some of the preferred features of the invention can be attained from a review of the following brief summary of a preferred version of the invention (depicted in the accompanying FIGS. 1 and 2), with more details being provided elsewhere in this document.

Referring to FIGS. 1 and 2, an electroporation chamber 100 has a housing defined by a first inlet/outlet port 102, a second inlet/outlet port 104, and an intermediate channel 106 which serves as a fluid passage between the inlet/outlet ports 102 and 104. The first and second inlet/outlet ports 102 and 104, which are preferably conductive, have an interior passage (not shown) extending between an external side 108 (illustrated as being defined by a Luer fitting) and an opposing threaded chamber side 110 (visible in FIG. 2). As also seen in FIG. 2, the threaded chamber sides 110 are threadable into the threaded interior passage 112 of the channel 106 (which is nonconductive).

A conductive first electrode 114 and a conductive second electrode 116 (both shown in FIG. 2) are fit within the interior channel passage 112, and these are preferably generally flat members (shown in FIG. 2 as discs) which are perforated to define a number of apertures 118 between their opposing sides. Within each electrode, the apertures 118 are preferably of at least substantially uniform size and are regularly spaced in an ordered array, and thus the electrodes 114 and 116 may each be conveniently formed of a conductive mesh screen wherein the apertures 118 are defined within the interstices of the mesh. The electrodes 114 and 116 have average aperture sizes and configurations which are chosen so that when a cell-bearing fluid medium flows through the ports 102 and 104 and channel 106 (and thus through the electrodes 114 and 116), one electrode (referred to herein as a receiving electrode) passes cells which fall below a certain maximum size, and the other electrode (referred to herein as a capturing electrode) will then catch and maintain these cells. Thus, the apertures 118 of the electrodes 114 and 116 are preferably sized on the order of a biological cell, and for the purposes of most electroporation procedures, the apertures 118 will have an average size of less than ½ mm$^2$. For purposes of the discussion below, it will be assumed that the first electrode 114 adjacent the first inlet/outlet port 102 has a larger mesh configured to pass cells of a desired size (and that the first electrode 114 therefore serves as a receiving electrode), whereas the second electrode 116 adjacent the second inlet/outlet port 104 has a smaller mesh configured to retain these cells (and therefore serves as a capturing electrode).

The electrodes 114 and 116 are connected to a power source 120 (depicted schematically in FIG. 1), usually a pulser capable of precisely generating waveforms with desired profiles, whereby they are chargeable to induce dielectric breakdown in the membranes of cells between the electrodes (i.e., to induce electroporation). As depicted in FIG. 1, such connection may be made via the inlet/outlet ports 102 and 104, which are in conductive contact with the electrodes 114 and 116. Within the interior channel passage 112, the first and second electrodes 114 and 116 are spaced by a resiliently compressible spacer 122, depicted in FIG. 2 as a nonconductive elastomeric ring (Teflon being a preferred material). Thus, when the electrodes 114 and 116 are situated on opposite sides of the spacer 122 within the interior channel passage 112, and the chamber sides 110 of the first and second inlet/outlet ports 102 and 104 are threaded into the interior channel passage 112 to each bear against a respective electrode, the inlet/outlet ports 102 and 104 urge the electrodes 114 and 116 towards each other to respace them, with the spacer 122 compressing therebetween. Alternatively, as the inlet/outlet ports 102 and 104 are threaded out of the interior channel passage 112, the spacer 122 urges the electrodes 114 and 116 apart and against the chamber sides 110 of the inlet/outlet ports 102 and 104. Thus, the electrodes 114 and 116 can be respaced as desired by adjusting the threaded inlet/outlet ports 102 and 104 with respect to the threaded channel 106, with the spacer 122 maintaining the electrodes 114 and 116 in spaced relationship as it compresses and expands.

The electroporation chamber 100 may be used as follows. First and second electrodes 114 and 116 may be chosen which have aperture sizes appropriate for the cells to be treated by an electroporation procedure, and the channel 106 and inlet/outlet ports 102 and 104 may be threadably adjusted to attain the desired spacing between the electrodes 114 and 116. The cells to be subjected to electrotreatment may be carried by a carrier medium (generally some liquid medium suitable for maintaining cell viability) from a cell source (illustrated schematically at 200 in FIG. 1), through any intermediate conduits and/or devices (again illustrated schematically at 210), and into the first inlet port 102 and through the first (receiving) electrode 114. The cells may then be captured by the second (capturing) electrode 116 as the carrier medium flows out of the chamber 100 into receiving conduits and/or devices (illustrated schematically at 220). Owing to the regular array defined by the apertures 118 of the mesh of the second electrode 116, the captured cells will also be situated in an ordered array. The power supply may then supply appropriate pulses to the electrodes 114 and 116 to promote electroporation of the cells. Because the cells are in a regular ordered array, and are generally uniformly spaced from each of the electrodes 114 and 116, they are subjected to a substantially uniform electric field, and thus the cells are treated more homogeneously than if they were situated in an unordered condition. Further, because the cells are in predictable locations, the ease of automated cell manipulation (e.g., via micromanipulators and the like) and cell diagnosis and imaging might be greatly enhanced. If desired, prior to electroporation, the flow of carrier medium may be replaced with promoter media for enhancing electroporation (e.g., liquids having lower conductivity); similarly, after a pulse or series of pulses, treatment media (e.g., liquids bearing exogenous materials) may be introduced into the channel 106 to flow to the cells. After treatment is complete, the cells may be readily recovered from the chamber 100 (if desired) by simply reversing the flow direction of the media so that the treated cells flow back through the receiving electrode 114 to the cell source 200.

Further advantages, features, and objects of the invention will be apparent from the following detailed description of the invention in conjunction with the associated drawings.

DETAILED DESCRIPTION OF PREFERRED VERSIONS OF THE INVENTION

Figure 2:
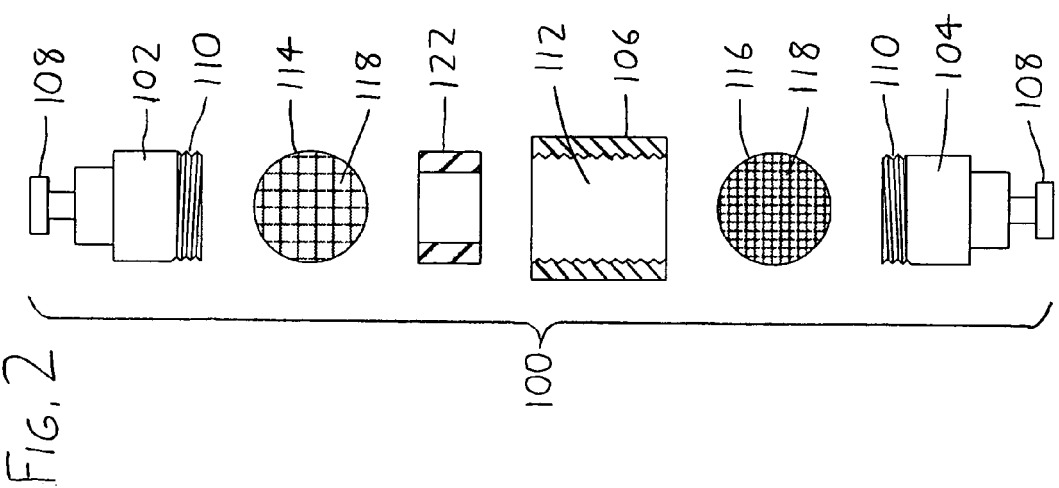
FIG. 2 is an exploded view of the electroporation chamber 100 of FIG. 1, wherein the channel 106 and spacer 122 are shown as cross-sections, and wherein the electrodes 114 and 116 are rotated 90 degrees so that their faces (which are ordinarily oriented perpendicularly to the longitudinal/flow axis of the electroporation chamber 100) are fully visible.

It should be understood that the version of the invention described in the Summary above is merely an exemplary preferred one, and numerous modifications to the electroporation chamber 100 are also considered to be within the scope of the invention. Following is an exemplary list of such modifications.

First, the housing of the electroporation chamber 100 can be constructed in numerous ways different from those shown. The inlet/outlet ports 102 and 104, the channel 106, and the electrodes 114 and 116 may take configurations which are different from the one illustrated; some of these components may be combined into an integral form; and/or some of these components might be omitted entirely. As one example, the intermediate channel 106 might be omitted, and one or both of the inlet/outlet ports 102 and 104 might be configured with a nonconductive outer shell which effectively takes the place of the intermediate channel 106. As another example, one or both of the electrodes 114 and 116 might be integrally formed with an inlet/outlet port 102 and 104, or with the channel 106.

Second, the first and/or second electrode 114 and 116 need not take the form of a mesh screen, and could instead take the form of a perforated plate or other foraminated structure. A structure which does not use an ordered array of apertures 118 is also possible, e.g. one or both electrodes 114 and 116 could be formed of nonwoven wire cloth, or a plate formed of sintered metal beads. However, ordered arrays of apertures 118 are preferred (at least for the capturing electrode) for the reasons noted above. Ordered arrays of apertures 118 are also preferred because with proper charging of the electrodes 114 and 116, they display useful dielectrophoretic effects: cells, which are poorly polarizable, are urged from regions of high electric field strength (such as in the areas immediately adjacent the boundaries of the apertures 118) so that they levitate adjacent the apertures of the capturing electrode. Thus, if the apertures 118 are in an ordered array, the levitated cells will similarly form an ordered two-dimensional lattice wherein the cell placements mimic the placements of the apertures 118 of the capturing electrode. Such levitation is useful because it reduces pressure and friction between the cells and the electrodes, thereby reducing cell stress and facilitating rotational reorientation of the cells (e.g., by an oscillating vibratory input, such as that described in U.S. Pat. No. 6,661,575 to Yakovenko).

Figure 1:
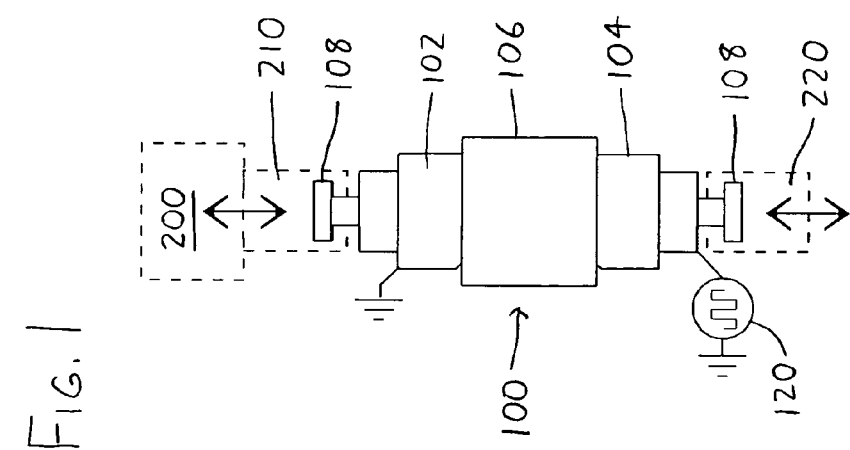
FIG. 1 is a side elevational view of an exemplary assembled electroporation chamber 100 showing a possible arrangement for its operation, wherein the first inlet/outlet port 102 of the chamber 100 receives cells (as well as any cell transport or other media) from a cell source 200 and an intermediate conduit/device 210 to perform electroporation or other operations on the cells within the chamber 100, with expelled media then being received by receiving conduit/device 220.

Third, one or both electrodes 114 and 116 might be formed of a nonconductive material (such as perforated structures formed of ceramics, plastics, or other dielectric materials), with the electric field being indirectly applied to the cells by its conductive inlet/outlet ports 102 and 104. The arrangement of FIGS. 1 and 2, wherein the electrodes 114 and 116 are in electrical communication with the inlet/outlet ports 102 and 104 to which the power supply 120 is connected, is a preferred one because the electrodes 114 and 116 provide a more uniform electric field across the passage and promote homogeneous treatment of all cells, whereas electric field emission from the ports 102 and 104 alone may result in varying field strengths across the fluid passage. A more preferred arrangement of this nature might be to form one or both of the first and second electrodes 114 and 116 of nonconductive materials, but then also provide a conductive lattice adjacent to the nonconductive electrode, with the conductive lattice serving to emits a relatively uniform field through the nonconductive electrodes 114 and 116.

Fourth, the inlet/outlet ports 102 and 104 need not themselves be conductive, and electrical communications could be supplied directly to the electrodes 114 and 116 themselves (e.g., by forming the inlet/outlet ports 102 and 104 of nonconductive materials, and having leads extend through them from the power supply 120 to the electrodes 114 and 116). The arrangement of FIGS. 1 and 2, wherein the first and second electrodes 114 and 116 are freely insertable within the intermediate channel 106 and are then powered by the inlet/outlet ports 102 and 104, is nonetheless preferred because this allows for easy replacement of electrodes 114 and 116 having differently-sized and/or differently-ordered apertures 118.

Fifth, the spacer 122 need not be formed of a compressible washer, and could instead be formed of other compressible structures. It could also or additionally be formed of a noncompressible structure which always maintains the electrodes 114 and 116 spaced at a predetermined distance. It is also possible that the spacer 122 might be entirely eliminated, and the electrodes 114 and 116 might be maintained in spaced relationship by other arrangements (e.g., by affixation to the inlet/outlet ports 102 and 104).

Sixth, the electroporation chamber 100 could be constructed with apertures 118 in only one of the electrodes 114 and 116, and the other non-perforated electrode could simply serve as a conventional electrode through which cells and media do not pass. As an example, with reference to FIGS. 1 and 2, the first electrode 114 might lack apertures 118, and cell-carrying media might then (for example) flow in through the side of the channel 106 and the spacer 122, with the cells then being captured on the perforated second electrode 116. As an alternative, cell-carrying media might flow through a perforated first receiving electrode 114, with the cells then resting adjacent to a nonperforated second electrode 116, and with the media possibly flowing through one or more exit ports extending through the side of the channel 106 which are sized to prevent the escape of cells.

The invention is not intended to be limited to the examples described above, but rather is intended to be limited only by the claims set out below. Thus, the invention encompasses all different versions that fall literally or equivalently within the scope of these claims.

What is claimed is:

1. An electroporation chamber comprising:
a. spaced first and second electrodes, wherein the electrodes are respaceable;
b. a power source connected to the electrodes;
c. a house defining a fluid passage along which the first and second electrodes are spaced, whereby fluid may flow between the electrodes; and
d. a threaded member adjustable with respect to the housing to respace the electrodes,
wherein at least one of the electrodes is perforated with apertures, with fluid flow within the fluid passage being directed through the perforated electrode.

2. The electroporation chamber of claim 1 wherein both electrodes are perforated with apertures.

3. The electroporation chamber of claim 2 wherein one of the electrodes has an average aperture size different from the average aperture size of the other electrode.

4. The electroporation chamber of claim 2 wherein:
a each electrode has apertures have at least substantially uniform size which are regularly spaced in an ordered array; and
b. one of the electrodes has an average aperture size different from the average aperture size of the other electrode.

5. The electroporation chamber of claim 1 wherein the apertures have an average size of less than ½ mm².

6. The electroporation chamber of claim 1 wherein the electrodes are spaced by a resilient compressible spacer.

7. The electroporation chamber of claim 1 wherein the fluid passage is defined by a channel having threading defined along at least a portion of its interior.

8. The electroporation chamber of claim 7 wherein at least one of the electrodes is situated within the interior of the fluid passage.

9. The electroporation chamber of claim 1:
a. further comprising a cell source in fluid communication with the portion of the fluid passage situated between the electrodes, and
b. wherein any cells provided by the cell source must pass through an electrode in order to reach the portion of the fluid passage situated between the electrodes.

10. An electroporation chamber comprising:
a. a first electrode, the first electrode having apertures of at least substantially uniform size defined therein;
b. a second electrode spaced from the first electrode, the second electrode having apertures of at least substantially uniform size defined therein, wherein the apertures of the second electrode have an average size different from the average aperture size of the first electrode;
c. a housing defining a fluid passage along which the first and second electrodes are situated, whereby fluid may flow through the first electrode and between the electrodes;
d. a cell source in fluid communication with the portion of the fluid passage situated between the electrodes;
wherein at least one of the electrodes is connected to a power source whereby it is chargeable to a potential different than that of the other electrode the power source supplying pulses sufficient to promote electroporation of cells situated between the electrodes.

11. An electroporation chamber comprising:
a. a first electrode, the first electrode having apertures defined therein:
(1) of at least substantially uniform size, and
(2) regularly spaced in an ordered array;
b. a second electrode spaced from the first electrode, the second electrode having apertures defined therein:
(1) of at least substantially uniform size,
(2) regularly spaced in an ordered array, and
(3) sized differently than the apertures of the first electrode;
c. a power source connected to the electrodes; and
d. a house defining a fluid passage along which the first and second electrodes are situated, whereby fluid is directed to flow between and through the electrodes;
wherein at least one of the electrodes is respaceable with respect to the other electrode.

12. The electroporation chamber of claim 11 wherein the electrodes are each defined by a conductive screen.

13. The electroporation chamber of claim 11 further comprising:
a. a resilient compressible spacer situated between the electrodes;
b. a threaded member adjustable to urge at least one of the electrodes toward the spacer.

14. The electroporation chamber of claim 11 wherein:
a. the fluid passage is defined by a channel having threading defined along at least a portion of its interior;
b. at least one of the electrodes is situated within the interior of the channel; and
c. a resilient compressible spacer is situated between the electrodes.

15. The electroporation chamber of claim 11 wherein the apertures of at least one of the electrodes are sized on the order of the size of a biological cell.

16. The electroporation chamber of claim 11 wherein at least one of the electrodes is respaceable with respect to the other electrode such that the distance between the electrodes is continuously adjustable.

17. The electroporation chamber of claim 1 wherein each perforated electrode has apertures which are regularly spaced in an ordered array.

18. The electroporation chamber of claim 10 wherein at least one of the electrodes is continuously respaceable with respect to the other electrode.

19. The electroporation chamber of claim 18 further comprising a resilient compressible spacer situated between the electrodes.

20. The electroporation chamber of claim 18 further comprising a threaded member adjustable to urge at least one of the electrodes toward the spacer.

* * * * *